United States Patent [19]

von Daehne et al.

[11] 4,315,004
[45] Feb. 9, 1982

[54] FUSIDIC ACID DERIVATIVES

[75] Inventors: Welf von Daehne, Rungsted Kyst; Poul R. Rasmussen, Frederikssund, both of Fed. Rep. of Germany

[73] Assignee: Leo Pharmaceutical products Ltd. A/S, Ballerup, Denmark

[21] Appl. No.: 44,163

[22] Filed: May 31, 1979

Related U.S. Application Data

[63] Continuation-in-part of Ser. No. 906,664, May 16, 1978, which is a continuation of Ser. No. 744,978, Nov. 24, 1976, Pat. No. 4,100,276.

[30] Foreign Application Priority Data

Dec. 3, 1975 [GB] United Kingdom .............. 49714/75
Apr. 20, 1976 [GB] United Kingdom .............. 16015/76

[51] Int. Cl.³ .................... A01N 45/00; A61K 31/56; C07J 9/00
[52] U.S. Cl. ................................. 424/238; 260/397.1
[58] Field of Search ........................................ 424/238

[56] References Cited

U.S. PATENT DOCUMENTS 4,004,004 1/1977 Von Daehne .................... 260/397.1
4,100,276 7/1978 Von Daehne et al. .......... 260/397.1

Primary Examiner—Elbert L. Roberts
Attorney, Agent, or Firm—Cushman, Darby & Cushman

[57] ABSTRACT

A method for treating arthritis which comprises administering to a subject in need of such treatment an effective amount of a fusidic acid derivative selected from compounds of the formula I:

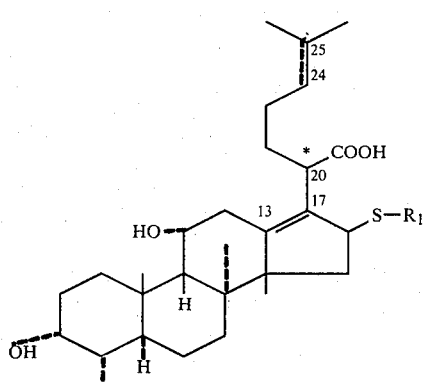

in which $R_1$ stands for a straight or branched alkyl radical having from 1 to 12 carbon atoms, and pharmaceutically acceptable, non-toxic salts and easily hydrolyzable esters thereof, and salts of such esters. The pure diastereomers as well as mixtures thereof may be used in carrying out the invention.

5 Claims, No Drawings

FUSIDIC ACID DERIVATIVES

This is a continuation-in-part of Ser. No. 906,664, filed May 16, 1978, which is a continuation of Ser. No. 744,978, filed Nov. 24, 1976, now U.S. Pat. No. 4,100,276. The subject matter of Ser. No. 906,664 and U.S. Pat. No. 4,100,276 is incorporated herein by reference.

U.S. Pat. No. 4,100,276 and Ser. No. 744,978 describe a new series of fusidic acid derivatives which possess antimicrobial and pharmacological properties. The present invention is based on the finding that certain of the fusidic acid derivatives of U.S. Pat. No. 4,100,276 and Ser. No. 906,664 exhibit antiarthritic properties and, therefore, may be used in the treatment of arthritis, particularly rheumatoid arthritis.

Broadly defined, the present invention comprises a method of treating arthritis, particularly rheumatoid arthritis, characterized by administering to a subject in need of such treatment, including humans, an effective amount of a fusidic acid derivative selected from the group consisting of compounds of the formula I:

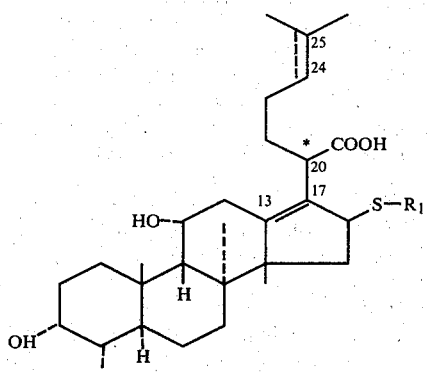

in which $R_1$ stands for a straight or branched alkyl radical having from 1 to 12 carbon atoms, such as methyl, ethyl, propyl, isopropyl, butyl, isobutyl, tert-butyl, the known isomers of pentyl, hexyl, heptyl, octyl and dodecyl, such alkyl radicals being optionally substituted with halogen atoms or hydroxy, alkyloxy, aralkyloxy, aryloxy, alkanoyloxy, aralkanoyloxy, aroyloxy, sulfhydryl, alkylthio, aralkylthio, arylthio, alkanoylthio, aroylthio, azido, nitro, cyano, thiocyano, hydroxycarbonyl, alkyloxycarbonyl, aryloxycarbonyl, amino, alkylamino, dialkylamino, arylamino, alkanoylamino, and aroylamino groups; $R_1$ can further be an alkenyl or alkynyl radical having from 3 to 6 carbon atoms, such as allyl, crotyl or propargyl, a cycloalkyl radical having from 3 to 7 carbon atoms in the alicyclic ring, such as cyclopropyl, cyclobutyl, cyclopentyl, cyclohexyl, cycloheptyl, or the mono- or dihalo, lower alkyl, lower alkoxy or hydroxy substituted analogues, an aralkyl or aryl radical, such as benzyl, phenylethyl, phenyl, furfuryl or naphthyl, optionally substituted with halogen, lower alkyl, hydroxy or alkoxy radicals; $R_1$ can also be a heterocyclic radical having 5 to 6 ring atoms and containing oxygen, sulphur and/or nitrogen atoms, such as 2- or 3-pyrryl, 2- or 3-furyl, 2- or 3-thienyl, 2-, 3- or 4-pyridyl, 2-, 4- or 5-pyrimidyl, 2- or 3-pyrazolyl, imidazolyl e.g. 1-methyl-2-imidazolyl, triazolyl, e.g. 5-methyl-1,2,4-triazol-3-yl, tetrazolyl e.g. 1-methyl-1H-tetrazol-5-yl, thiazolyl, thiadiazolyl e.g. 5-methyl-1,3,4-thiadiazol-2-yl, and in which formula I the dotted line between C-24 and C-25 indicates that the carbon atoms in question are connected by either a double bond or a single bond, and the asterisk at C-20 indicates that the compounds exist in two diastereomeric forms; pharmaceutically acceptable, non-toxic salts and easily hydrolysable esters thereof. If the ester moiety contains acidic ar basic groups, salts of such esters are also included. The pure diastereomers as well as mixtures thereof may be used in carrying out the invention.

According to the invention, it has been found that the indicated fusidic acid derivatives have antiarthritic properties, function in a manner generally similar to those demonstrated by the antiarthritic drugs D-penicillamine and Levamisole and show specific activity against rheumatoid arthritis.

For many years the objective of much research into the drug treatment of rheumatic disease has been the development of better ways of suppressing inflammation. This goal has been achieved with the use of inhibitors of prostaglandin synthetase like aspirin, indomethacin, etc. and/or with the use of compounds able to interfere with the fibrinolytic systems as for instance the compounds described in U.S. Pat. No. 3,920,817. This approach has made little impact on rheumatoid arthritis, a disease which appears to be more appropriately treated with drugs like D-penicillamine or Levamisole. Drugs of this latter type are not only more effective than antiinflammatory drugs, but, with long term therapy, they may alter the eventual outcome of the disease. For this reason D-penicillamine and Levamisole are called "specific drugs for rheumatoid arthritis" to distinguish them from "non-specific" or symptomatic remedies like analgesic and anti-inflammatory drugs.

D-penicillamine and Levamisole fail to show any effect on the experimental models used to screen antiinflammatory agents. However, they have been shown able to enhance cell-mediated immune responses. There is some evidence that these responses are depressed in patients with rheumatoid arthritis, and it has been postulated that the chronicity of inflammation in rheumatoid arthritis may be maintained by the persistence of a foreign antigen and/or by the inability of an individual to remove or conceal it. In these circumstances it is as logical to stimulate the appropriate cells to respond to and eliminate the antigen as it is to suppress the immunological reaction which represents the efferent loop of the pathway.

In the search for drugs endowed with D-penicillamine-like activity, i.e. activity which is specific for rheumatoid arthritis a major problem is the choise of appropriate experimental assays. In fact, D-penicillamine and Levamisole have no effect on common models of acute inflammation such as carrageenin edema which are suppressed by aspirin-like drugs. Consideration has been given to two experimental models of immunologically mediated inflammation the intensity of which has been reported in the literature to be enhanced by D-penicillamine and Levamisole.

The first of these models is the rat adjuvant arthritis, an experimental disease, produced by the injection of Freund's complete adjuvant into the subdermal tissues of a hind paw. A local reaction develops immediately; a few days later the contralateral paw and the fore paws swell. This secondary reaction is termed "adjuvant arthritis", and it represents a delayed hypersensitivity to the injected antigens. The measurement of the magnitude of swelling of the non-injected hind paw provides an objective assessment of the intensity of the reaction.

The second experimental model is the Pertussis vaccine reaction. The injection of Pertussis microorganisms into the subdermal tissues of a hind paw of previously sensitized rats elicits a reaction delayed in onset caused by a cell-mediated immune response. The intensity of the response can be quantitated measuring the swelling of the paw.

Using the above-mentioned experimental models with the preferred compounds of the invention, with D-penicillamine, Levamisole, and with two compounds according to U.S. Pat. No. 4,004,004 (fusidic acid derivatives known to have an antiarthritic activity), gave the results shown in tables I and II. In these tables the code numbers used have the following meanings:

| Code No. | Compound according to Example No. |
| --- | --- |
| PR 1089 | 9, 25 |
| PR 1099 | 13 |
| PR 1126 | 29 |
| PR 1127 | 19 |
| PR 1132 | 14 |
| PR 1136 | 23 |
| PR 1141 | 10 |
| PR 1154 | 20 |
| PR 1234 | 12 |
| PR 1251 | 27, 31 C |
| PR 1254 | 31 D |
| VD 1313* | 3 A |
| VD 1314* | 4 A |

* = compounds according to examples of U.S. Pat. No. 4,004,004.

Table I

| | Adjuvant arthritis | | | |
| --- | --- | --- | --- | --- |
| | Daily oral dose | No. of | Swelling of the non-injected paw ml ± S.E. | |
| Compound | mg/kg | rats | on day 14 | on day 28 |
| Control | | 12 | 0.72 ± 0.10 | 1.48 ± 0.19 |
| D-Penicillamine | 50 | 12 | 1.61 ± 0.28* | 2.12 ± 0.22* |
| Levamisole | 10 | 10 | 1.52 ± 0.26* | 2.18 ± 0.24* |
| PR 1089 | 10 | 15 | 0.83 ± 0.21 | 1.73 ± 0.15 |
| PR 1089 | 50 | 12 | 1.14 ± 0.19* | 2.21 ± 0.13* |
| PR 1089 | 100 | 12 | 1.36 ± 0.24* | 2.51 ± 0.29* |

Table I-continued

| | Adjuvant arthritis | | | |
| --- | --- | --- | --- | --- |
| | Daily oral dose | No. of | Swelling of the non-injected paw ml ± S.E. | |
| Compound | mg/kg | rats | on day 14 | on day 28 |
| PR 1099 | 50 | 8 | 1.12 ± 0.11* | 1.85 ± 0.11* |
| PR 1126 | 50 | 8 | 1.21 ± 0.15* | 1.78 ± 0.13* |
| PR 1127 | 50 | 8 | 1.19 ± 0.12* | 1.91 ± 0.15* |
| PR 1132 | 50 | 8 | 1.01 ± 0.23 | 1.96 ± 0.09* |
| PR 1136 | 50 | 8 | 1.29 ± 0.12* | 1.67 ± 0.15 |
| PR 1141 | 50 | 8 | 0.98 ± 0.12 | 1.88 ± 0.12* |
| PR 1154 | 50 | 8 | 1.07 ± 0.23 | 1.81 ± 0.08* |
| PR 1234 | 50 | 8 | 1.14 ± 0.19* | 1.98 ± 0.11* |
| PR 1251 | 50 | 8 | 1.15 ± 0.17* | 2.01 ± 0.16* |
| PR 1254 | 50 | 8 | 1.12 ± 0.07* | 2.05 ± 0.15* |
| VD 1313 | 50 | 6 | 1.07 ± 0.13 | 1.88 ± 0.15* |
| VD 1314 | 50 | 8 | 1.14 ± 0.12* | 1.92 ± 0.11* |

* = p ≦ 0.05

Table I shows that the present compounds, like D-penicillamine and Levamisole, enhances the intensity of the reaction when orally administered to rats from the day of Freund's complete adjuvant injection to 28 days later.

As mentioned before, the swelling of the non-injected paw (i.e. the secondary reaction) represents the delayed hypersensitivity reaction to the injected antigen. The enhancement of the swelling in treated animals as compared to control animals suggests that the present compounds, like D-penicillamine and Levamisole are able to stimulate the ability of the animals to react to the foreign antigen.

In the second experimental assay (Pertussis vaccine reaction) the compounds have been given either around the day of the sensitization or around the day of the challenge. In both the cases an enhancement of the reaction in the treated animals—as assessed measuring the swelling of the challenged paw—has been observed (see Table II). These results suggest that the compounds of the invention, like D-penicillamine and Levamisole stimulate cell-mediated immune reactions.

VD 1313 and VD 1314 fail to enhance or just marginally enhance the intensity of the reaction when administered according to the above dosing regimes.

Table II

| | Pertussis vaccine reaction | | | | |
| --- | --- | --- | --- | --- | --- |
| | Daily oral dose | Dosing | No. of | Swelling, ml ± S.E. hours after challenge | |
| Compound | mg/kg | regimes | rats | 24 | 72 |
| Control | | | 22 | 1.02 ± 0.11* | 0.79 ± 0.18 |
| D-Penicillamine | 50 | from day 3 | 12 | 1.49 ± 0.14* | 1.47 ± 0.15* |
| Levamisole | 10 | before to | 10 | 1.39 ± 0.11* | 1.31 ± 0.10* |
| PR 1089 | 25 | day 1 | 12 | 1.29 ± 0.12* | 1.25 ± 0.12* |
| PR 1089 | 50 | after the | 12 | 1.35 ± 0.15* | 1.34 ± 0.13* |
| PR 1127 | 50 | challenge | 8 | 1.18 ± 0.13 | 1.28 ± 0.12* |
| PR 1234 | 50 | | 8 | 1.23 ± 0.21 | 1.29 ± 0.11* |
| PR 1251 | 50 | | 8 | 1.26 ± 0.13* | 1.29 ± 0.12* |
| PR 1254 | 50 | | 8 | 1.24 ± 0.11* | 1.21 ± 0.12* |
| VD 1313 | 50 | | 6 | 1.09 ± 0.12 | 1.07 ± 0.22 |
| VD 1314 | 50 | | 6 | 1.18 ± 0.21 | 1.22 ± 0.09* |
| D-Penicillamine | 50 | from day 4 | 15 | 1.18 ± 0.14* | 1.19 ± 0.11* |
| Levamisole | 10 | before to | 12 | 1.22 ± 0.10* | 1.15 ± 0.09* |
| PR 1089 | 25 | day 4 | 15 | 1.29 ± 0.15* | 1.19 ± 0.08* |
| PR 1089 | 50 | after the | 15 | 1.34 ± 0.11* | 1.27 ± 0.12* |
| PR 1127 | 50 | sensiti- | 8 | 1.18 ± 0.11* | 1.15 ± 0.19 |
| PR 1234 | 50 | zation | 8 | 1.16 ± 0.21 | 1.19 ± 0.11* |
| PR 1251 | 50 | | 8 | 1.21 ± 0.09* | 1.16 ± 0.09* |
| PR 1254 | 50 | | 8 | 1.19 ± 0.14* | 1.20 ± 0.11* |

Table II-continued

| | Pertussis vaccine reaction | | | | |
|---|---|---|---|---|---|
| | Daily oral dose | Dosing | No. of | Swelling, ml ± S.E. hours after challenge | |
| Compound | mg/kg | regimes | rats | 24 | 72 |
| VD 1313 | 50 | | 6 | 1.12 ± 0.12 | 1.19 ± 0.07* |
| VD 1314 | 50 | | 6 | 0.97 ± 0.11 | 1.03 ± 0.18 |

* = p <0.01

The similarity of the effects of the compounds of the invention with those of D-penicillamine and Levamisole in two different assays of immunologically mediated inflammation is remarkable and shows that the compounds of the present invention have in common with the two other drugs the ability to stimulate some of the compounds of cell-mediated immune reactions. This ability is likely to be relevant in the beneficial effects of D-penicillamine and Levamisole in rheumatoid arthritis where cell-mediated immune defects do exist.

An important difference between the present compounds and the previously described VD 1313 and VD 1314 is the poor effect of the latter compounds in one of the experimental models used, i.e. the Pertussis vaccine reaction, suggesting difference in the mode of action.

It is also noted that PR 1089 has been administered to 12 rheumatoid arthritic patients (disease in functional stage 2-3) who had to discontinue previous treatment with D-penicillamine or Levamisole either because of lack of efficacy or because of serious side-effects. After six months of treatment with doses increasing, at fortnight steps from 125 mg to 500–750 mg daily, 9 out of 12 patients showed improvement of the clinical conditions as assessed by subjective and objective criteria and laboratory parameters for disease activity. No side-effects were observed.

As previously mentioned, it is known that some fusidic acid derivatives show an antiarthritic activity, cf. U.S. Pat. Nos. 3,920,817 and 4,004,004. However, the compounds according to U.S. Pat. No. 3,920,817 show no statistically significant activity when tested in the two above-mentioned experimental models this lack of activity presumably due to a different mode of action, whereas the compounds according to U.S. Pat. No. 4,004,004 show only a moderate activity in the two above-mentioned experimental models, cf. the above results.

As indicated, fusidic acid derivatives for use according to the invention are compounds of the formula I:

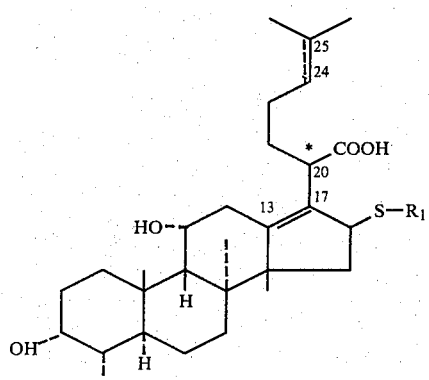

in which $R_1$ stands for straight or branched alkyl or alkenyl with from 2 to 6 carbon atoms, for phenyl-lower alkyl or for furyl-lower alkyl.

More particularly, the fusidic acid derivative used herein may be a compound of formula I in which $R_1$ stands for branched alkyl with from 3 to 6 carbon atoms, or for benzyl, phenethyl or furfuryl.

Most particularly, the fusidic acid derivative used herein may be a compound of formula I in which $R_1$ stands for isopropyl, or benzyl.

Where not otherwise stated the term alkyl in the radicals mentioned above stands for a $C_1$ to $C_4$ alkyl radical.

The compounds of formula I can be used as such or in the form of salts or esters, or salts of the esters, as defined above. The salts are especially the pharmaceutically acceptable, non-toxic salts, such as alkali metal salts and alkaline earth metal salts, for example, sodium, potassium, magnesium or calcium salts, as well as salts with ammonia or suitable non-toxic amines, e.g. lower alkylamines, for example, triethylamine, hydroxylower alkylamines, for example, 2-hydroxyethylamine, bis-(2-hydroxyethyl)-amine or tri-(2-hydroxyethyl)-amine, cycloalkylamines, for example, dicyclohexylamine, or benzylamines, for example, N,N'-dibenzyl-ethylenediamine or dibenzylamine.

The easily hydrolysable esters can e.g. be of the type alkanoyloxyalkyl, aralkanoyloxyalkyl, aroyloxyalkyl or alkoxy-carbonyloxyalkyl esters, such as acetoxymethyl, pivaloyloxymethyl, benzoyloxymethyl esters, and the corresponding 1'-oxyethyl derivatives, methoxycarbonyloxymethyl, ethoxycarbonyloxymethyl and the corresponding 1'-oxyethylderivatives; lactonyl esters, such as phthalidyl esters; or dialkylaminoalkyl esters, such as diethylaminoethyl esters. The salts of the esters containing an acidic or basic group in the ester moiety are formed with pharmaceutically acceptable, non-toxic bases and acids, such as the above mentioned bases and hydrohalide acids, sulfuric acid, nitric acid, phosphoric acid, and carboxylic acid, such as acetic acid, maleic acid, organic sulfonic acids, e.g. p-toluenesulfonic acids.

A particularly preferred compound according to the invention is the fusidic acid derivative prepared as the sodium salt in example 9 below. Preparation of the same compound, either in salt or free acid form, is also described in examples 25, 27 and 31. For convenience of reference, this preferred compound is given the designation PR 1089 in the ensuing description.

The compounds of formula I can be prepared, as described in U.S. Pat. No. 4,100,276 and Ser. No. 906,664.

Suitable compositions for use according to the invention are also described in U.S. Pat. No. 4,100,276 and in Ser. No. 906,664. Broadly defined, these compositions comprise at least one fusidic acid derivative selected from the group consisting of compounds of formula I, salts thereof with non-toxic, pharmaceutically acceptable bases, and esters thereof as described above, together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as granules, tablets, pills, dragees, suppositories, capsules, sustained-release tablets, suspensions or injection medicine. Pharmaceutical organic or inorganic, solid or liquid carriers and/or diluents suitable for oral, enteral, or parenteral administration can be used to make up compositions containing the present compounds. Water, gelatine, lactose, starch, magnesium stearate, talc, vegetable and animal oils and fats, benzyl alcohol, gum, polyalkylene glycol, cocoa butter, or other known carriers for medicaments are all suitable, while stabilizing agents, wetting and emulsifying agents, salts for varying the osmotic pressure or buffers for securing an adequate pH-value of the composition can be used as auxiliary agents.

The compositions may further contain other therapeutically active compounds, for instance a compound, or compounds, selected from e.g. the group of drugs commonly used in the treatment of arthritis. Also the composition may in addition to the compounds of the invention contain symptom relieving drugs commonly used in the treatment of patients suffering from arthritis, e.g. muscle relaxantia and analgesic agents.

Examples of drugs for the treatment of arthritis and to be used in the present composition together with one or more compounds of the formula I include, but are not limited to the following: glucocorticoids, such as cortisone, hydrocortisone, prednisone or prednisolone, methylprednisolone, triamcinolone, fluprednisolone, parametasone, betametasone and dexametasone; ATCH; antiinflammatory agents, e.g. pyrazolidine derivatives, such as phenyl butazone; indol derivatives, such as indometacin; benzydamine; aromatically substituted organic acids, such as salicylic acid and esters thereof, and aromatically substituted acetic acids, such as naproxen; and antranilic acid derivatives; chloroquine and derivatives thereof; anti-rheumatic gold preparations; preparations for use against gouty arthritis, such as allopurinol, probenecid, and colchicine.

Examples of muscle relaxants include, but are not limited to, the following: chlorzoxazone, methocarbamol, and diazepam.

Examples of suitable analgesic agents include, but are not limited to, the following: morfinomimetics, dextropropoxiphene, salicylic acid and derivatives thereof, and codein.

For granules, tablets, capsules or dragees the pharmaceutical composition of the invention appropriately contain from 25 percent to 95 percent of the active substance of the invention, and in oral suspensions the corresponding amount is appropriately from 2–25 percent.

For parenteral use the compounds of the invention are preferably given by injection of pharmaceutical compositions containing from 1 to 20 percent of the active ingredient.

When the compounds of formula I are administered in the form of salts with pharmaceutically acceptable, non-toxic bases, the preferred salts are for instance the sodium salts or the diethanolamine salts, but other pharmaceutically acceptable and non-toxic salts may be used.

Another object of the invention resides in the selection of a dose of the compounds of the invention which dose can be administered so that the desired activity is achieved without simultaneous secondary effects. In human therapy, the compounds of the invention are conveniently administered (to adults) in dosage units containing not less than 50 mg and up to 1000 mg, preferably from 250 to 750 mg, calculated as a compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

In the form of a dosage unit, the compound may be administered once or more times a day at appropriate intervals, always depending, however, on the condition of the patient, and in accordance with the prescription made by the medical practitioner.

Thus in systemic treatment a daily dose will be from 0.25 g to 5 g per day, preferably an amount of from 0.5 to 3 g, calculated as a compound of formula I.

If the composition is to be injected, a sealed ampoule, a vial or a similar container may be provided containing a parenterally acceptable aqueous or oily injectable solution or dispersion of the active material as the dosage unit.

In the continuous therapy of patients suffering from arthritis, tablets or capsules may be the appropriate form of pharmaceutical preparation owing to the prolonged effect obtained when the drug is given orally, in particular in the form of sustained-release tablets.

It is contemplated that the method of the invention will normally require administering to patients from 0.25 g to 5 g per day, preferably from 0.5 to 3 g per day, calculated as a compound of the formula I, or an equivalent amount of a salt or an ester as defined before of a compound of the formula I. Preferably, the compound is given in the form of the dosage units aforesaid.

The invention will be further described in the following examples which are not to be construed as limiting the invention.

EXAMPLE 1

3α,11α-Dihydroxy-16β-phenylthiofusida-13(17),24-dien-21-oic acid sodium salt

To an icecooled solution of 3-acetyl-16-epideacetylfusidic acid benzyl ester (15 g; 25 mmol) and diphenyldisulfide (13.5 g, 62 mmol) in dry pyridine (100 ml) was added tributylphosphine (30 ml; 126 mmol), and the mixture was left at 5° C. After 3 days, additional amounts of diphenyldisulfide (3.4 g, 16 mmol) and tributylphosphine (7.5 ml; 31.5 mmol) were added, and after a total period of 5 days at 5° C. a mixture of dimethylsulfoxide (100 ml) and 30 percent aqueous sodium hydroxide (50 ml) was added, and the resulting suspension was heated to 70° C. for 3 hours. After cooling to 20° C., ether (1 liter), water (3 liter), and saturated aqueous sodium chloride (100 ml) was then added with stirring causing the desired product to precipitate as colourless crystals. After 1 hour of stirring, the organic phase containing the crystals was filtered, and the crystals were washed with water (100 ml) and ether (200 ml), and dried to yield 3α,11α-dihydroxy-16β-phenylthiofusida-13(17),24-dien-21-oic acid sodium salt as a mixture of the two C-20-isomers; melting point 243°–247° C.

Found: C 63.65, H 8.62, S 4.84, H$_2$O 10.4%. C$_{35}$H$_{49}$NaO$_4$S,4H$_2$O Requires: C 63.59, H 8.69, S 4.85, H$_2$O 10.9%.

EXAMPLE 2

The sodium salt of 3α,11α-dihydroxy-16β-(4′-bromophenylthio)fusida-13(17),24-dien-21-oic acid Following the procedure of Example 1 and substituting di-(4-bromophenyl)disulfide for diphenyldisulfide, 3α,11α-dihydroxy-16β-(4′-bromophenylthio)fusida-13(17),24-dien-21-oic acid sodium salt was obtained as a mixture of the two C-20 -isomers; melting point 231°–239° C.

Found: C 61.67, H 7.63, S 4.83, Br 11.24%. C$_{35}$H$_{48}$NaBrO$_4$S, H$_2$O requires: C 61.30, H 7.35, S 4.68, Br 11.66%.

EXAMPLE 3

The sodium salt of 3α,11α-dihydroxy-16β-(2′,5′-dichlorophenylthio)fusida-13(17),24-dien-21-oic acid Following the procedure of Example 1 and substituting di(2,5-dichlorophenyl)disulfide for diphenyldisulfide, 3α,11α-dihydroxy-16β-(2′,5′-dichlorophenylthio)fusida-13(17),24-dien-21-oic acid sodium salt was prepared, as a crystalline product with no well-defined melting point. (The product is a mixture of the two C-20-isomers).

EXAMPLE 4

The sodium salt of 3α,11α-dihydroxy-16β-phenylthiofusida-13(17),24-dien-21-oic acid 16-Epideacetylfusidic acid benzyl ester (3 g, 5.3 mmol) and diphenyldisulfide (4.9 g, 23 mmol) were dissolved in pyridine (20 ml), the solution was cooled to 0° C., and tributylphosphine (5.5 ml, 23 mmol) was added. After standing at 20° C. for 3 days, the solution was diluted with ether (100 ml), washed with 4 N hydrochloric acid (2×25 ml), with 2 N sodium hydroxide (2×25 ml) and with water (2×50 ml), dried, and evaporated in vacuo to yield crude 16-deacetoxy-16β-phenylthiofusidic acid benzyl ester as an oil. This residue was dissolved in a mixture of dimethylsulfoxide (200 ml) and 2 N aqueous sodium hydroxide (50 ml). After heating for 3 hours at 70° C., ether (100 ml) and water (200 ml) was slowly added to the reaction mixture to precipitate the desired product as colourless crystals. The ethereal phase, containing the crystals, was filtered, and the crystals were washed with water and ether, and dried to afford the sodium salt of 3α,11α-dihydroxy-16β-phenylthiofusida-13(17),24-dien-21-oic acid in the form of a mixture of the two C-20-isomers; melting point 243°–247° C.

EXAMPLES 5–7

Following the procedure of Example 4 and substituting the disulfides listed in table III for diphenyldisulfide, the 16β-thioethers of 3α,11α-dihydroxyfusida-13(17),24-dien-21-oic acid sodium salt in table III were prepared as mixtures of the two C-20-isomers.

Table III

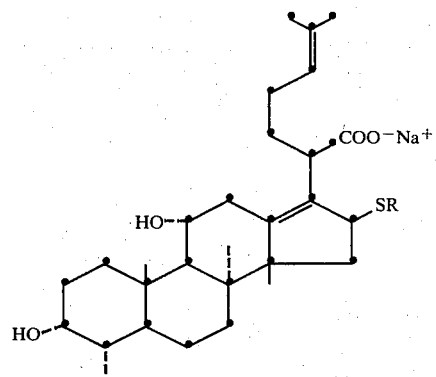

| Example | Disulfide | Resulting compound R | Mp (°C.) |
|---|---|---|---|
| 5 | Di(o-methylphenyl) | o-CH$_3$ . C$_6$H$_4$ | 222–238 |
| 6 | Di(m-methylphenyl) | m-CH$_3$C$_6$H$_4$ | 226–234 |
| 7 | Di(p-methylphenyl) | p-CH$_3$C$_6$H$_4$ | 199–213 |

EXAMPLE 8

3α,11α-Dihydroxy-16β-phenylthiofusida-13(17)-en-21-oic acid, sodium salt.

To an icecooled mixture of 16-epideacetyl-24,25-dihydrofusidic acid benzyl ester (6.2 g, 11 mmol) and diphenyldisulfide (6.3 g, 29 mmol) was added tributylphosphine (14 ml, 59 mmol), and the mixture was left at 20° C. for 48 hours. 40 ml of dimethylsulfoxide and 20 ml of 30 percent aqueous sodium hydroxide were then added, and the resulting suspension was heated to 70° C. for two hours. After cooling to 20° C., ethyl ether (200 ml) and water (600 ml) were added. After some hours the desired product precipitated as colourless crystals. After 24 hours at room temperature, the organic phase containing the crystals was filtered, and the crystals were washed with water (100 ml) and ethyl ether (100 ml), and dried to yield the sodium salt of 3α,11α-dihydroxy-16β-phenylthiofusida-13(17)-en-21-oic acid as a mixture of the two C-20-isomers. This crude product was recrystallized from methanol-water giving the analytically pure compound; melting point 235°–241° C.

EXAMPLE 9

The sodium salt of 3α,11α-dihydroxy-16β-isopropylthiofusida-13(17),24-dien-21-oic acid To a solution of potassium hydroxide (10 g; 150 mmol) and isopropyl mercaptan (30 ml; 320 mmol) in pure ethanol (750 ml) was added 3-acetyl-16-deacetoxy-16α-bromofusidic acid benzyl ester (24 g; 36 mmol), and the resulting solution was left at room temperature for 3 days. Thereafter, the major part of ethanol was removed in vacuo, and to the residue was added ethyl acetate (200 ml) and water (100 ml). The organic phase was separated, washed twice with water, dried, and evaporated in vacuo to yield crude 3-acetyl-16-deacetoxy-16β-isopropylthiofusidic acid benzyl ester as an oily residue.

This residue was dissolved in a mixture of 30 percent aqueous sodium hydroxide (40 ml) and dimethylsulfoxide (200 ml). After heating for 3 hours at 70° C., water (1000 ml) and ether (200 ml) was added with stirring. After 1 hour, the organic phase containing the desired product as colourless crystals was separated, the crystals were filtered of, washed with water and ether, and dried to yield 3α,11α-dihydroxy-16β-isopropylthiofusida-13(17),24-dien-21-oic acid sodium salt as a mixture of the two C-20-isomers.

Recrystallization from methanol-water gave the analytical sample, melting point 220°–228° C.

Found: C 61.68, H 9.32, S 5.14%. C$_{32}$H$_{51}$O$_4$SNa, 4H$_2$O requires: C 61.31, H 9.49, S 5.12%.

EXAMPLES 10–24

16β-Thioethers of 3α,11α-dihydroxy-fusida-13(17),24-dien-21-oic acid sodium salt Following the procedure of Example 5 and substituting the mercaptans listed in table IV for isopropyl mercaptan, the 16β-thioethers of 3α-11α-dihydroxy-fusida-13(17),24-dien-21-oic acid sodium salt listed in table III were prepared as mixtures of the two C-20-isomers.

Table IV

| Example | Mercaptan | Resulting compound R | Mp (°C.) |
|---|---|---|---|
| 10 | methyl mercaptan | CH$_3$ | 252–262 |
| 11 | ethyl mercaptan | CH$_2$CH$_3$ | 201–210 |
| 12 | n-butyl mercaptan | (CH$_2$)$_3$—CH$_3$ | 136–145 |
| 13 | tert-butyl mercaptan | C(CH$_3$)$_3$ | 222–235 |
| 14 | allyl mercaptan | CH$_2$CH=CH$_2$ | 175–200 |
| 15 | cyclohexyl mercaptan | cyclohexyl | >250 |
| 16 | n-heptyl mercaptan | (CH$_2$)$_6$—CH$_3$ | 196–210 |
| 17 | n-dodecyl mercaptan | (CH$_2$)$_{11}$—CH$_3$ | 116–136 |
| 18 | thiophenol | C$_6$H$_5$ | 243–247 |
| 19 | benzyl mercaptan | CH$_2$C$_6$H$_5$ | 210–222 |
| 20 | 2-phenylethyl-mercaptan | CH$_2$CH$_2$C$_6$H$_5$ | 234–242 |
| 21 | 4-tert-butyl-thiophenol | 4-C$_6$H$_4$C(CH$_3$)$_3$ | 215–225 |
| 22 | thio-2-naphthol | 2-naphthyl | 145–165 |
| 23 | furfuryl mercaptan | 2-furfuryl | 216–221 |
| 24 | 2-pyridyl mercaptan | 2-pyridyl | 216–221 |

EXAMPLE 25

3α,11α-Dihydroxy-16β-isopropylthiofusida-13(17),24-dien-21-oic acid sodium salt

To a solution of 3-O-acetyl-16-deacetoxy-16α-bromofusidic acid benzyl ester (33.5 g, 50 mmol) in 75 ml of dimethylsulfoxide was added a solution of sodium hydroxide (2.4 g, 60 mmol) and isopropyl mercaptan (1 ml, 75 mmol) in 25 ml of ethanol. After stirring at room temperature for 2 hours, 30 percent aqueous sodium hydroxide (25 ml) was added, and the resulting mixture was heated to 70° C. for 2 hours. After cooling to 20° C., water (500 ml), 4-methyl-2-pentanone (500 ml), and 4 N aqueous hydrogen chloride (400 ml) were added. The organic phase was collected, washed with water, and filtered. The resulting solution was stirred, while 2 N aqueous sodium hydroxide (100 ml) was slowly added causing the desired product to precipitate as colourless crystals. After cooling to 5° C. for 2 hours, the crystals were filtered off, washed with water (2×10 ml) and 4-methyl-2-pentanone (2×10 ml), and dried to yield analytically pure 3α,11α-dihydroxy-16β-isopropylthiofusida-13(17),24-dien-21-oic acid sodium salt as a mixture of the two C-20-isomers; melting point 243°–248° C.

EXAMPLE 26

3α,11α-Dihydroxy-16β-isopropylthiofusida-13(17)-en-21-oic acid sodium salt

Following the procedure of Example 25 and substituting 3-O-acetyl-16-deacetoxy-24,25-dihydro-16α-bromofusidic acid benzyl ester for the corresponding 24,25-unsaturated compound, 3α,11α-dihydroxy-16β-isopropylthiofusida-13(17)-en-21-oic acid was prepared as a crystalline sodium salt; melting point 215°14 240° C. (dec.).

EXAMPLE 27

3α,11α-Dihydroxy-16β-isopropylthiofusida-13(17),24-dien-21-oic acid

The sodium salt of 3α,11α-dihydroxy-16β-isopropylthiofusida-13(17),24-dien-21-oic acid (10 g), prepared as described in Example 25, was dissolved in methanol (150 ml), and 1 N aqueous hydrochloric acid (17,5 ml) was added. The resulting solution was stirred at 20° C., while 22.5 ml of water was slowly added causing the desired product to crystallize. After stirring for 2 hours, the crystals were filtered off, washed with methanol-water (4/1), and dried to yield 7.0 g of a mixture of the two C-20-isomers of 3α,11α-dihydroxy-16β-isopropylthiofusida-13(17),24-dien-21-oic acid, melting point 130°–134° C.; $[\alpha]_D^{20} = -92.9°$ (C=1, chloroform). To the mother liquor 10 ml of water was added, causing an additional amount of only one of the two isomers to precipitate as colourless crystals, which were collected and recrystallized from methanol-water to give one of the two C-20-isomeric acids (360 mg) in a pure state, melting point 109°–113° C. $[\alpha]_D^{20} = -37.8°$ (C=1, chloroform).

(This product is identical with that of Example 31C).

EXAMPLE 28

3α,11α-dihydroxy-16β-(2′-aminoethylthio)fusida-13(17),24-dien-21-oic acid

A.

3-Acetyl-16-deacetoxy-16β-(2′-aminoethylthio)fusidic acid benzyl ester

3-Acetyl-16-deacetoxy-16α-bromofusidic acid benzyl ester (2.68 g; 4 mmol) was added to a solution of potassium hydroxide (8.64 g; 130 mmol) and the hydrochloride of cystein amine (9.0 g; 80 mmol) in 150 ml of pure ethanol. After stirring for 16 hours at room temperature, water (200 ml) was slowly added to crystallize the desired compound.

The crystals were filtered off, washed with a mixture of water (10 ml) and ethanol (10 ml), and dried to yield 3-acetyl-16-deacetoxy-16β-(2′-aminoethylthio)fusidic acid benzyl ester (2.49 g); melting point 150°–173° C.

Recrystallization from methanol-water gave the analytical sample, melting point 184°–186° C.

Found: C 71.61, H 8.92, S 4.81, N 2.04%. C$_{40}$H$_{59}$O$_5$NS requires: C 72.15, H 8.93, S 4.81, N 2.10%.

B.
3α,11α-dihydroxy-16β-(2'-aminoethylthio)fusida-13(17),24-dien-21-oic acid 600 mg of the above benzyl ester was dissolved in a mixture of dimethylsulfoxide (50 ml) and 2 N aqueous sodium hydroxide (10 ml). After heating to 70° C. for 1.5 hour, water (250 ml) was added. Adjustment of the pH-value to 6.0 by addition of 4 N aqueous hydrochloric acid caused an amorphous product to precipitate. This crude product was filtered off, dried and dissolved in boiling ethyl acetate (150 ml). When this solution was allowed to cool to room temperature with stirring, an amorphous precipitate was formed. The 3α,11α-dihydroxy-16β-(2'-aminoethylthio)fusida-13(17),24-dien-21-oic acid thus obtained was filtered off, and dried to yield a mixture of the two C-20 isomers.

Found: C 65.80, H 9.54, S 5.59, N 2.40%.
$C_{31}H_{51}NO_4S$ requires: C 65.34, H 9.73, S 5.63, N 2.46%.

The NMR spectrum ($CD_3OD$) shows signals at $\delta = 0.96$ (d, 3H), 1.01 (s, 3H), 1.21 (bs, 6H), 1.59 and 1.65 (2 bs, 6H), 2.5–3.4 (m, 4H; $-SCH_2CH_2N^\oplus H_3$), 3.61 (m, 1H; C$\underline{H}$-3), 3.78 (m, 1H; C$\underline{H}$-20), 4.31 (m, 1H; C$\underline{H}$-11) and 5.13 (m, 1H; C$\underline{H}$-24) ppm. Tetramethylsilane was used as internal reference.

EXAMPLE 29

3α,11α-dihydroxy-16β-(2'-hydroxyethylthio)fusida-13(17),24-dien-21-oic acid

A. 3-Acetyl-16-deacetoxy-16β-(2'-hydroxyethylthio) fusidic acid benzyl ester

3-Acetyl-16-deacetoxy-16α-bromofusidic acid benzyl ester (1.34 g, 2 mmol) was added to a solution of potassium hydroxide (1.68 g, 25 mmol) and 2-hydroxyethyl mercaptan (2.1 ml, 30 mmol) in 150 ml of pure ethanol. After stirring for 16 hours at room temperature, water (100 ml) was added slowly to crystallize the desired compound. The crystals were filtered off, washed with a mixture of water (5 ml) and methanol (5 ml), and dried to yield 3-acetyl-16-deacetoxy-16β-(2'-hydroxyethylthio)fusidic acid benzyl ester (1.18 g); melting point 167°–176° C.

Recrystallization from methanol-water raised the melting point to 175°–178° C.

B.
3α,11α-dihydroxy-16β-(2'-hydroxyethylthio)fusida-13(17),24-dien-21-oic acid 700 mg of the above benzyl ester was dissolved in a mixture of dimethylsulfoxide (50 ml) and 2 N aqueous sodium hydroxide (10 ml). After heating to 70° C. for 1.5 hour, the mixture was acidified with 4 N hydrochloric acid (pH=2, and water (100 ml) and ether (100 ml) was added. The organic phase was separated, washed with water (5×50 ml), dried, and evaporated in vacuo to give an oily residue, containing the two isomers of the desired product. This residue was separated into two fractions by dry column chromatography on silica gel (cyclohexan:chloroform:acetic acid, 10:80:10).

The more polar of these two fractions separated by dry column chromatography contained one of the two C-20-isomers of 3α,11α-dihydroxy-16β-(2'-hydroxyethylthio)fusida-13(17),24-dien-21-oic acid (290 mg) and the less polar contained 50 mg of the other isomer. The NMR spectrum ($CDCl_3$) of the more polar C-20-isomer shows signals at 1.00 (s, 3H), 1.21 (bs, 3H), 1.25 (s, 3H), 1.61 and 1.69 (2 bs, 6H), 2.75 (m, 2H, $CH_2S$), 3.5–3.9 (m, 5H, CH-3, CH-16, CH-20 and $CH_2OH$), 4.40 (m, 1H, CH-11) and 5.06 (m, 1H, CH-24) ppm. Tetramethylsilane was used as internal reference.

The NMR spectrum ($CD_3OD$) of the less polar C-20-isomer shows signals at 0.86 (d, J=7, 3H), 0.97 (s, 3H), 1.13 (s, 3H), 1.20 (s, 3H), 1.56 and 1.61 (2 bs, 6H), 2.62 (m, 2H, $SCH_2$), 3.5–3.8 (m, 5H, CH-3, CH-16, CH-20 and $CH_2OH$), 4.27 (m, CH-11) and 5.15 (m, 1H, CH-24) ppm. Tetramethylsilane was used as internal reference.

EXAMPLE 30

Separating the two C-20-isomers of 3α,11α-dihydroxy-16β-phenylthiofusida-13(17),24-dien-21-oic acid A suspension of the sodium salt of 3α,11α-dihydroxy-16β-phenylthiofusida-13(17),24-dien-21-oic acid (1 g of the mixture of isomers prepared according to Example 1) in a mixture of ether (50 ml) and 1 N aqueous hydrochloric acid (10 ml) was shaken until the crystals had disappeared. The organic phase was separated, washed twice with water, dried, and evaporated in vacuo. The residue was dissolved in 5 ml of boiling cyclohexane. Upon cooling to room temperature, a crystalline product separated, which was filtered off, washed with 1 ml of cyclohexane and dried. Recrystallization from 5 ml of cyclohexane yielded one of the two C-20-isomers in a pure state with melting point 96°–98° C.

The mother liquor was evaporated in vacuo and the residue was crystallized from ether-petroleum ether to yield 210 mg of the other C-20-isomer, purified by recrystallization from ether-petroleum ether to show a melting point of 94°–99° C. According to thin layer chromatography (Solvent system: chloroform:cyclohexane:methanol:acetic acid, 80:10:2.5:10; spray reagent: Sulphuric acid) the latter product is the less polar of the two isomers.

EXAMPLE 31

Separating the two C-20-isomers of 3α,11α-dihydroxy-16β-isopropylthiofusida-13(17),24-dien-21-oic acid A. One C-20-isomer of 3α-O-formyl-11α-hydroxy-16β-isopropylthiofusida-13(17),24-dien-21-oic acid acetoxymethylester The sodium salt of 3α,11α-dihydroxy-16β-isopropylthiofusida-13(17),24-dien-21-oic acid, as prepared in Example 25 (1.5 g, 2.5 mmol) was dissolved in dimethylformamide (15 ml) and chloromethyl acetate (0.3 ml, 3.3 mmol) was added. After standing for 16 hours at 20° C., the reaction mixture was cooled to 0° C. and stirred while thionylchloride (1 ml, 13.7 mmol) was slowly added. After stirring for one hour at 20° C. ethyl ether (100 ml) was added and the resulting mixture was washed with water (4×50 ml), dried and evaporated to yield 1.4 g. of a mixture of the two C-20-isomeric esters. This residue was dissolved in petroleum ether (15 ml) and upon scratching one of the two isomers crystallized in a pure state. The crystals were collected, washed with petroleum ether and dried to yield the desired compound, melting point 126°–128° C.

B. The other isomer of 3α-O-formyl-11α-hydroxy-16β-isopropylthiofusida-13(17),24-dien-21-oic acid acetoxymethyl ester.

The mother liquor from the crystallization of the compound of part A of this Example was evaporated in vacuo, and the residue was purified by chromatography on silica gel (cyclohexane:ethyl acetate, 8:2) to give the desired compound as an oily residue.

C. One C-20-isomer of 3α,11α-dihydroxy-16β-isopropylthiofusida-13(17),24-dien-21-oic acid.

The compound of part A of this Example (300 mg) was dissolved in methanol (15 ml), potassium carbonate (300 mg) was added, and the mixture was stirred at room temperature for one hour. The reaction mixture was then evaporated in vacuo and ethyl ether (50 ml) and 1 N hydrochloric acid (25 ml) was added. The organic phase was separated, washed twice with water and evaporated to yield a crude product, which was crystallized from methanol/water to yield one isomer of 3α,11α-dihydroxy-16β-isopropylthiofusida-13(17),24-dien-21-oic acid, melting point 110°–112° C; $[\alpha]_D^{20} = -37.8°$ (C=1 in chloroform).

D. The other C-20-isomer of 3α,11α-dihydroxy-16β-isopropylthiofusida-13(17),24-dien-21-oic acid.

By following the procedure of part C of this Example but substituting the product of part B for that of part A the other isomer of 3α,11α-dihydroxy-16β-isopropythiofusida-13(17),24-dien-21-oic acid was prepared as colourless crystals, melting point 144°–149° C.; $[\alpha]_D^{20} = -158.7°$ (C=1 in chloroform).

EXAMPLE 32

3α,11α-Dihydroxy-16β-phenylthiofusida-13(17),24-dien-21-oic acid acetoxymethyl ester The sodium salt of 3α,11α-dihydroxy-16β-phenylthiofusida-13(17),24-dien-21-oic acid (330 mg, 0.5 mmol; the more polar of the two isomers, as separated in Example 26) was dissolved in 2 ml of dimethylformamide, and chloromethyl acetate (50 μl, 0.55 mmol) was added. After standing at room temperature for 16 hours, ether (50 ml) was added, and the resulting mixture was washed with water (4×50 ml), dried, and evaporated to yield 3α,11α-dihydroxy-16β-phenylthiofusida-13(17),24-dien-21-oic acid acetoxymethyl ester (one of the two possible C-20-isomers) as a colourless foam (180 mg).

The NMR spectrum (CDCl₃) shows signals at δ=0.88 (d, J=6, 3H), 0.97 (s, 3H), 1.16 (bs, 6H), 1.59 and 1.67 (2 bs, 6H), 2.02

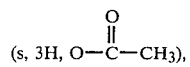
(s, 3H, O—C(=O)—CH₃), 3.52 (m, CH-20), 3.63 (m, CH-3), 4.16 (bd, CH-16), 4.29 (m, CH-11), 5.12 (m, CH-24), 5.67 and 5.81

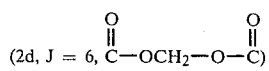
(2d, J = 6, C(=O)—OCH₂—O—C(=O))

and 7.1–7.5 (5 H, aromatic CH) ppm. Tetramethylsilane was used as internal reference.

EXAMPLE 33

3α,11α-Dihydroxy-16β-phenylthiofusida-13(17),24-dien-21-oic acid fusidyloxymethyl ester Following the procedure of Example 32 and substituting fusidic acid chloromethyl ester for chloromethyl acetate, 3α,11α-dihydroxy-16β-phenylthiofusida-13(17),24-dien-21-oic acid fusidyloxymethyl ester was prepared as a colourless foam.

EXAMPLE 34

Capsule

| | |
|---|---|
| 3α,11α-dihydroxy-16β-isopropylthio-fusida-13(17)-en-21-oic acid sodium salt | 250 g |
| Microcrystalline cellulose | 145 g |
| Magnesium stearate | 5 g |
| | 400 g |

Pass the ingredients through a 60 mesh sieve and mix for 10 minutes. Fill the mixture into hard gelatin capsules No. 00 (Parke Davis & Co.) using a capsule fil weight of 400 mg.

EXAMPLE 35

Preparation of tablets

| | |
|---|---|
| 3α,11α-dihydroxy-16β-isopropylthiofusida-13(17),24-dien-21-oic acid | 250 g |
| Avicel PH 101 | 120 g |
| STA-Rx 1500 | 120 g |
| Magnesium stearate | 10 g |

3α,11α-dihydroxy-16β-isopropylthiofusida-13(17),24-dien-21-oic acid, Avicel and STA-Rx are mixed together, sieved through a 0.7 mm sieve and thereafter mixed with the magnesium stearate. The mixture is pressed into tablets each of 500 mg.

EXAMPLE 36

Preparation of suspension

| | |
|---|---|
| 3α,11α-dihydroxy-16β-phenylthiofusida-13(17),24-dien-21-oic acid | 5.00 g |
| Citric acid | 0.45 g |
| Sodium monohydrogenphosphate | 0.70 g |
| Sucrose | 25.00 g |
| Tween 80 | 0.05 g |
| Potassium sorbate | 0.20 g |
| Carboxymethylcellulose-Na | 0.50 g |
| Purified water | qs to 100 ml suspension |

The crystals are micronized and suspended in a solution of the citric acid, the sodium monohydrogenphosphate, the sucrose, the potassium sorbate and the Tween 80 in 50 ml water, if necessary under slight warming. The carboxymethylcellulose-Na is dissolved in 20 ml of boiling water. After cooling, it is added to the other ingredients. The suspension is homogenized in a blender and finally purified water is added to a total volume of 100 ml.

Having described the invention what is claimed as new is:

1. A method for treating arthritis which comprises administering to a subject in need of such treatment an effective amount of a fusidic acid derivative selected from compounds of the formula I:

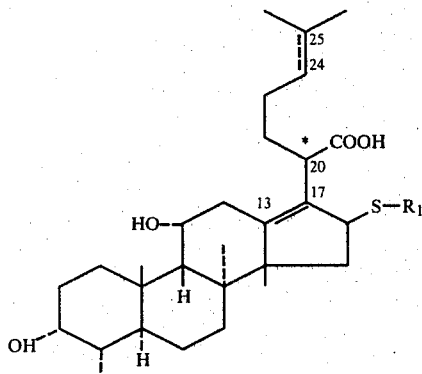

in which $R_1$ stands for straight or branched alkyl or alkenyl with from 2 to 6 carbon atoms, for phenyl-lower alkyl or for furyl-lower alkyl; or pharmaceutically acceptable, non-toxic salts and easily hydrolysable esters thereof, and pharmaceutically acceptable, non-toxic salts of such esters.

2. A method according to claim 1 in which $R_1$ in formula I stands for branched alkyl with from 3 to 6 carbon atoms, or for benzyl, phenethyl or furfuryl, or pharmaceutically acceptable, non-toxic salts and esters thereof, and pharmaceutically acceptable, non-toxic salts of such esters.

3. The method of claim 1 wherein the compound is $3\alpha,11\alpha$-dihydroxy-$16\beta$-isopropylthiofusida-13(17),24-dien-21-oic acid, or pharmaceutically acceptable, non-toxic salts or esters thereof or a pharmaceutically acceptable, non-toxic salt of such esters.

4. The method of claim 1 wherein the compound is $3\alpha,11\alpha$-dihydroxy-$16\beta$-benzylthiofusida-13(17),24-dien-21-oic acid, or pharmaceutically acceptable, non-toxic salts or esters thereof or a pharmaceutically acceptable, non-toxic salt of such ester.

5. A method according to claim 1 in which the therapeutically active compound is administered by the oral route, in amounts from 250 to 5000 mg per day, preferably from 500 to 3000 mg per day.

* * * * *

UNITED STATES PATENT AND TRADEMARK OFFICE
CERTIFICATE OF CORRECTION

PATENT NO. : 4,315,004
DATED : February 9, 1982
INVENTOR(S) : Welf von Daehne & Poul R. Rasmussen Page 1 of 3

It is certified that error appears in the above-identified patent and that said Letters Patent are hereby corrected as shown below:

On the title page
In the heading, correct Item [75] to read:

--Welf von Daehne, a citizen of Fed. Rep. of Germany, residing in Rungsted Kyst, Denmark; Poul R. Rasmussen, a citizen of Denmark, residing in Frederikssund, Denmark--

Correct Item [73] to read:

[73] Assignee: Leo Pharmaceutical Products Ltd. A/S (Løvens kemiske Fabrik Produktionsaktieselskab)

Column 12, line 19, delete "14" between "215°" and "240°C"

Column 13, line 67, underscore the "H" in "CH" to read as C$\underline{H}$

UNITED STATES PATENT AND TRADEMARK OFFICE
CERTIFICATE OF CORRECTION

PATENT NO. : 4,315,004

DATED : February 9, 1982

INVENTOR(S) : Welf von Daehne & Poul R. Rasmussen

It is certified that error appears in the above-identified patent and that said Letters Patent are hereby corrected as shown below:

Column 13, line 68, add underscoring as follows:

", C$\underline{H}$-3, C$\underline{H}$-16, C$\underline{H}$-20 and C$\underline{H}_2$OH)"

Column 14, line 1, underscore the "H" in "CH" (both occurrences) to read: "C$\underline{H}$-11" and "C$\underline{H}$-24"

line 6, underscore the "H" in "SC$\underline{H}_2$", "C$\underline{H}$-3", "C$\underline{H}$-16" and "C$\underline{H}$-20"

line 7, underscore the "H" in "C$\underline{H}_2$OH", "C$\underline{H}$-11" and "C$\underline{H}$-24"

Column 15, lines 50-51, in the formula, underscore the "H" in "C$\underline{H}_3$"

line 53, underscore the "H" in "C$\underline{H}$-20", "C$\underline{H}$-3" and "C$\underline{H}$-16"

UNITED STATES PATENT AND TRADEMARK OFFICE
CERTIFICATE OF CORRECTION

PATENT NO. : 4,315,004
DATED : February 9, 1982
INVENTOR(S) : Welf von Daehne & Poul R. Rasmussen It is certified that error appears in the above–identified patent and that said Letters Patent are hereby corrected as shown below:

Column 15, line 54, underscore the "H" in "CH-11" & "CH-24"
          line 60, underscore the "H" in "CH"

Signed and Sealed this

Twenty-first Day of December 1982

[SEAL]

Attest:

Attesting Officer

GERALD J. MOSSINGHOFF
Commissioner of Patents and Trademarks

UNITED STATES PATENT AND TRADEMARK OFFICE
CERTIFICATE OF CORRECTION

PATENT NO. : 4,315,004
DATED : February 9, 1982
INVENTOR(S) : Welf vonDaehne and Poul R. Rasmussen It is certified that error appears in the above-identified patent and that said Letters Patent are hereby corrected as shown below:

Column 1, in the formula (lines 24-39);

Column 5, in the formula (lines 52-68); and

Column 17, in the formula (at about line 15)

>    the broken line should go to the "O"
>
>    rather than the "H" of the "OH" substituent.

*Signed and Sealed this*

*Eighth* Day of *February 1983*

[SEAL]

*Attest:*

*Attesting Officer*

GERALD J. MOSSINGHOFF
*Commissioner of Patents and Trademarks*